United States Patent [19]

Richards

[11] 4,012,823
[45] Mar. 22, 1977

[54] METHOD OF MAKING ARTIFICIAL INTRAOCULAR LENSES

[75] Inventor: William Richards, Medway, Mass.

[73] Assignee: American Optical Corporation, Southbridge, Mass.

[22] Filed: Dec. 8, 1975

[21] Appl. No.: 638,489

[52] U.S. Cl. .................................. 29/418; 3/13; 29/525

[51] Int. Cl.² ...................................... B23P 17/00

[58] Field of Search ........... 29/525, 418, 423; 3/13; 140/93 R

[56] References Cited

UNITED STATES PATENTS

| 3,252,495 | 5/1966 | Waltermire | 29/525 X |
| 3,906,551 | 9/1975 | Otter | 3/13 |
| 3,911,516 | 10/1975 | Einhorn | 29/525 X |
| 3,971,073 | 7/1976 | Richards | 3/13 |

Primary Examiner—Richard B. Lazarus
Attorney, Agent, or Firm—Howard R. Berkenstock, Jr.; William C. Nealon

[57] ABSTRACT

A lens suitable for implantation in the eye is provided with iris clips of wire each having at least one end locked to the lens by an interference fit in an opening in the lens body. A leader of a cross-sectional size freely insertable through the opening is formed upon the wire, inserted through the opening and used to forcefully draw the adjacent full diameter portion of the wire into the lens to produce the interference fit. The leader is cut away and partial retraction of the thus fitted wire can be effected to recess its terminus.

8 Claims, 15 Drawing Figures

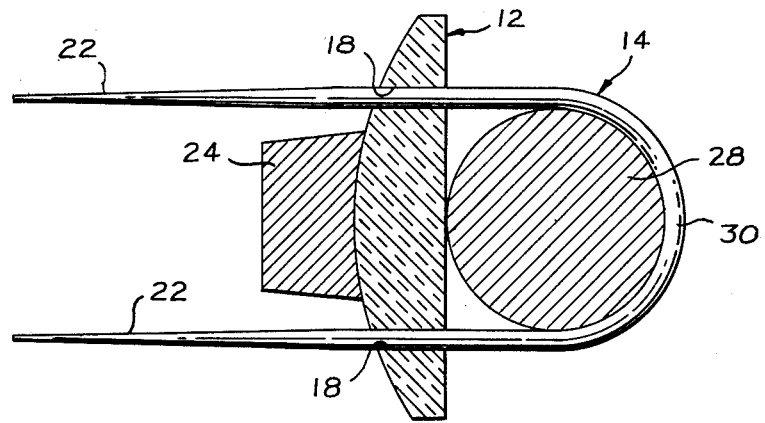
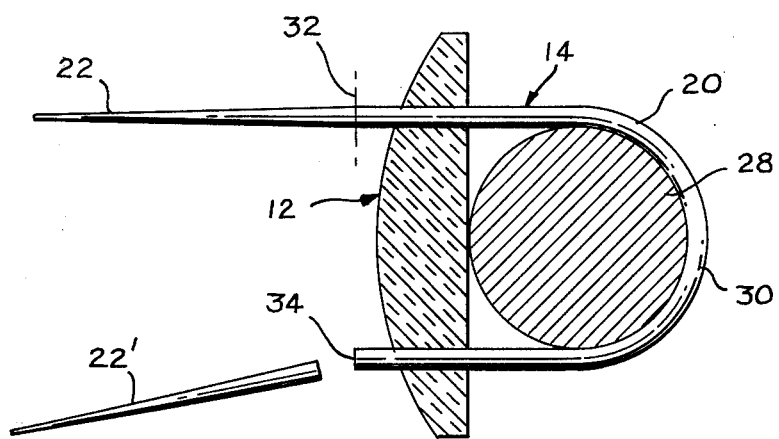
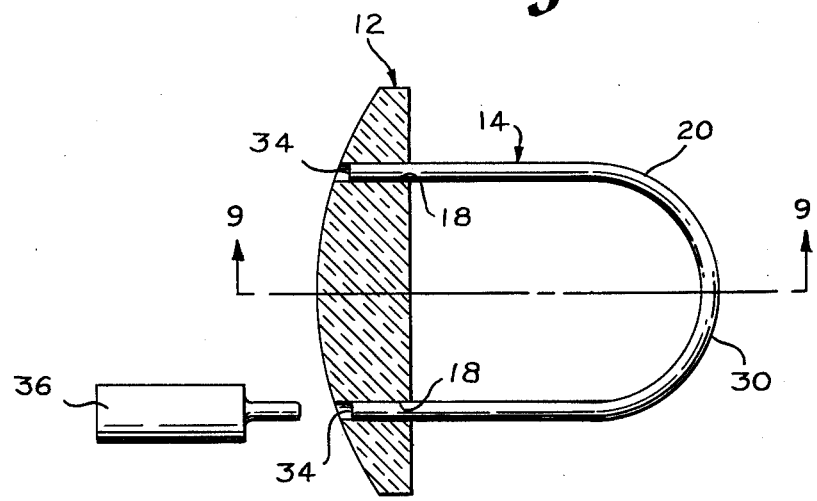

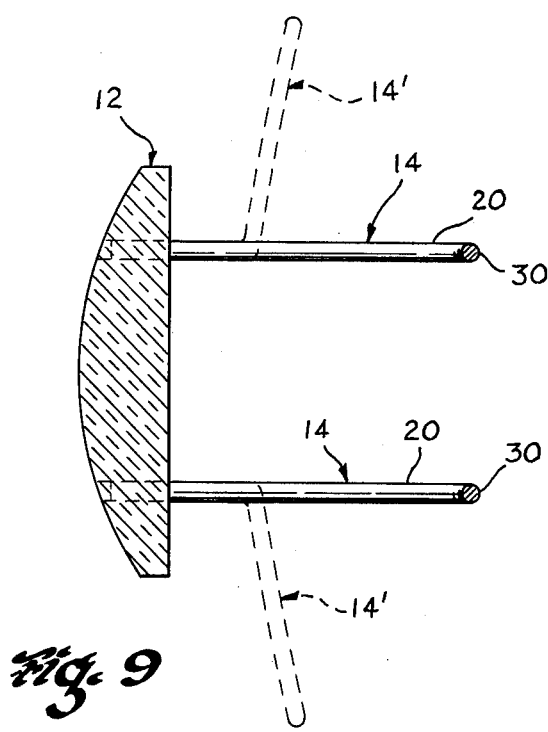
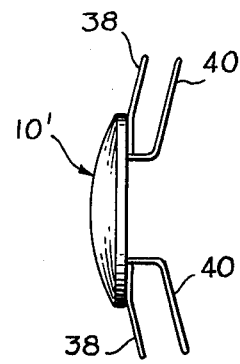
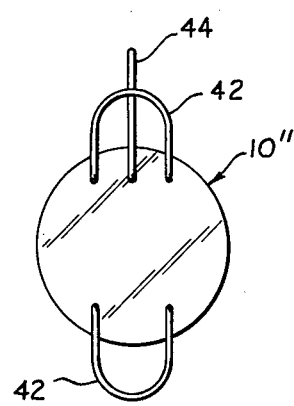
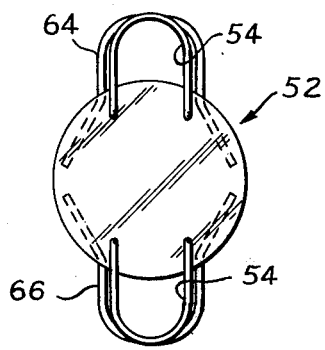
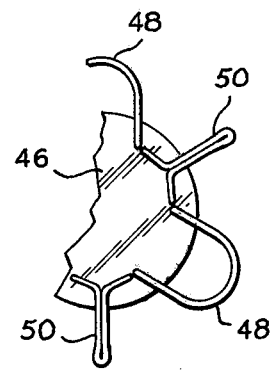
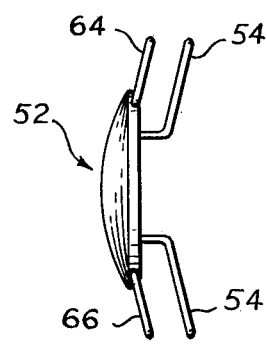
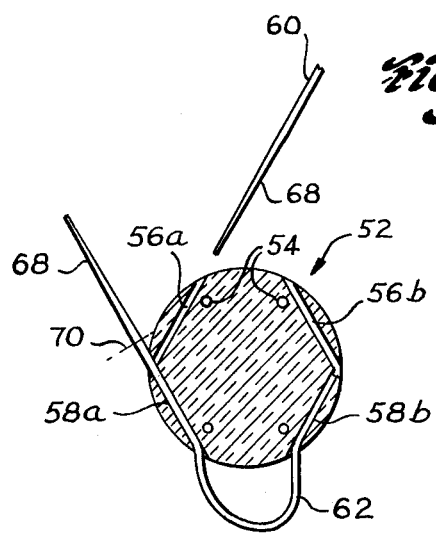

4,012,823

METHOD OF MAKING ARTIFICIAL INTRAOCULAR LENSES

BACKGROUND OF THE INVENTION

1. Field of the Invention

This invention relates to improvements in ophthalmology and more particularly to improvements in the manufacture of artificial intraocular lenses (pseudophakoi) used for the correction of aphakia and re-establishment of binocularity in aphakia.

2. Discussion of the Prior Art

Well-fixed and well-centered intraocular lens implants are known to produce stable retinal images with stable space localization and offer the best chance of re-establishment of binocularity in cases of aphakia.

Many techniques of lens implantation, including suturing to the ciliary muscle as disclosed in U.S. Pat. No. 3,711,870 and iris diaphragm fixation as disclosed in U.S. Pat. No. 3,673,616, for example, have been used. The latter is considered to be a safe procedure giving good stability and the present invention deals with improvements in this general type of pseudophakos. More particularly, the invention relates to improvements in "iridocapsular" and/or "iris clip" implants having a fastening section comprised of posterior and/or anterior haptic elements (iris clips) which may be in the form of loops or struts of wire or wire-like material.

Heretofore, the wires of iris clips have been fastened by extending ends thereof into holes drilled or otherwise formed in the lenses. Anchoring or locking these wires against accidental withdrawal and disconnection from the lens, however, has presented the serious problems of having to establish and maintain exacting tolerances of hole and wire size for fitting, the use and dependence upon adhesives or dealings with intricate and costly special tools and fixtures in attempts to avoid the use of adhesives by press-fitting.

The use of adhesive materials in pseudophakoi not only requires the provision of substances having strong bonding properties but further requires that they be biologically inert and resistant to absorption or deterioration by human body fluids. Under most, if not all, conditions, however, there remains the possibility of deterioration of the bonded components, if not the cement itself, or both, causing loosening or detachment of parts in the eye with prolonged use.

Press-fitting, on the other hand, eliminates the need for adhesives but requires exacting tolerances of hole and wire size which presents exceptional manufacturing problems. The minute size of anchoring hole and wire diameters required of pseudophakoi are alone problematic, not to mention the imposition of press-fitting tolerances. The tediousness of manufacture, its requirement for special jigs, fixtures, tools and skills together with current high scrap yield seriously limit present day output and contribute to high, if not excessive, product cost, all without assurance that loosening or disconnection of parts under usage will not occur. Furthermore, all pseudophakoi require a sturdiness of structure which is sufficient to withstand relatively harsh manipulation and adjustment of parts by the surgeon prior to and/or during implantation. Accordingly, an assurance against accidental disconnection of parts at this point in time as well as subsequent to implantation is of extreme importance and urgently sought in the art.

One solution to the problem of avoiding the use of adhesives and the need for special tolerances of wire fit is disclosed in a co-pending application of the present inventor which was filed on Sept. 22, 1975 and bears Ser. No. 615,275 and is assigned to the assignee of this application. This invention provides beads or similar enlargements upon the ends of pseudophakoi clips which are forced into the material of lenses receiving the same. Locking in situ is accomplished by a cold flow of material around the preformed beads or enlargements.

The present invention, however, is directed toward further simplification of procedure in the manufacture of pseudophakoi which, without the need for adhesives, undue hole and wire size tolerances or beaded wires, uniquely accomplishes an interference fit between lens and iris clips which provides a positive and dependable locking together of these parts. A further aim of the invention is to accomplish the foregoing objective with greater than usual ease and substantially less than usual product cost.

SUMMARY OF THE INVENTION

The aforesaid objectives and their corollaries are accomplished by effecting a dependably secure interference fit between lens clip wires and lens body material in holes provided through the body material of pseudophakoi without requiring exceptional tolerances of wire and hole size. Relatively large differences of wire and lens body hole diameters may be provided in the construction of lens and iris clip components of pseudophakoi according to the invention. Entrance of a relatively large diameter wire clip into a relatively small diameter anchoring hole to produce a desired secureness of interference fit is made possible by providing a leader of substantially reduced diametral dimension upon an end of a wire intended to be so fastened. The leader being freely insertable through a lens hole intended to receive the wire is "threaded" through the hole, gripped with suitable pulling means, e.g., a pair of pliers, and forcefully pulled to the point where the transition between reduced and full diameter emerges from the hole. The full diameter of the wire is thus brought into contact with the lens material throughout the full length of the receiving hole and an exceptionally tight interference fit is produced by virtue of the aforesaid preselected relatively large differential of hole and wire size. The leader is then cut away and discarded. Recessing of the cut end of remaining wire being preferable, it may be retracted slightly into the lens, e.g., with a punch. In the case of installing lens clips of the loop-type according to the invention, opposite ends of a single piece of wire will both be provided with leaders and assembled as described above.

Details of the invention will become more readily apparent from the following description when taken in conjunction with the accompanying drawings.

IN THE DRAWINGS

Figure 3:
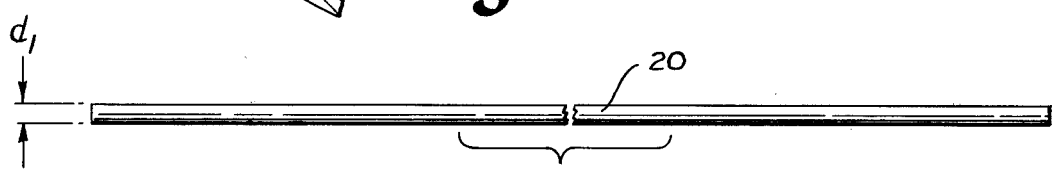
FIG. 3 is an elevational view of a wire intended to be used to form one haptic element (iris clip) of the pseudophakos.
Figure 4:

FIG. 4 illustrated a modification of the wire shown in FIG. 3 which is effected prior to its installation;

FIGS. 5, 6, 7 and 8 are illustrations, partly in cross-section, of steps followed in assembling the pseudophakos according to the invention;

FIG. 9 is a view, partially in cross-section, of the finally assembled structure and illustrates with broken lines, a final forming operation;

FIGS. 10, 11 and 12 illustrate some of many modified forms of pseudophakoi to which the present invention is applicable; and FIGS. 13, 14 and 15 illustrate in rear elevation, side elevation and partial cross-section respectively a still further modification of the invention.

DESCRIPTION OF THE PREFERRED EMBODIMENTS

Figure 1:
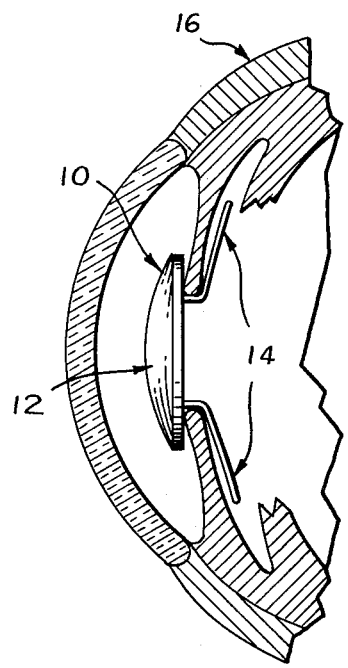
FIG. 1 is an illustration of a preferred embodiment of a pseudophakos in situ.

Referring more particularly to FIG. 1 of the drawings, there is shown a pseudophakos 10 of a type comprising lens 12 and a pair of posterior iris clips 14 for fixturing within eye 16. This form of pseudophakos, which is shown for purposes of illustration only, is commonly referred to as an "iridocapsular lens" or "two-loop lens". Its fixation is in the iridocapsular cleft substantially as illustrated in FIG. 1.

Lens 12 is formed of a material which is biologically inert, i.e., not susceptible to being absorbed by body fluids and capable of being well tolerated by the human body when implanted. Exemplary materials are ophthalmic glasses which are free of toxic and/or radioactive ingredients and methylmethacrylate resins such as those available under the tradenames "Lucite" and "Plexiglass" or biologically neutral chemically pure polymethylmethacrylates and biologically inert polymeric materials.

Iris clips 14 which comprise loops of wire having their opposite ends secured to lens 10 are, for reasons of avoiding irritation and/or human body rejection, formed of a biologically inert material such as platinum, titanium, tantalum or an extruded polyamide such as nylon or one of the other aforementioned plastic materials and combinations thereof.

Iris clips 14 and others to be mentioned hereinafter will be referred to as being "wire" or "formed of wire". Accordingly, it should be understood that the term "wire" as used in this specification and its appended claims is intended to include strands, strips, rods or fibers of biologically inert material whether the material is metallic or plastic and whether one or both is used to make up a particular array of iris clips.

Figure 2:
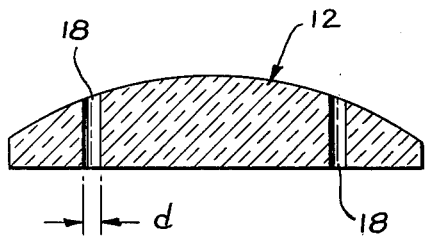
FIG. 2 is an enlarged cross-sectional view of the optical portion (lens) of the pseudophakos.

The technique for securing clips 14 to lens 12 according to the present invention is illustrated in FIGS. 3–8 and involves the following procedure:

Lens 12 is provided with anchoring openings or holes 18 (FIG. 2) of a predetermined diametral dimension $d$.

Each iris clip 14 is formed of wire 20 (FIG. 3) which is of a preselected length, e.g., 25 mm or whatever may be sufficient to produce the full extent of reach desired of a clip 14 when subsequently looped from one of holes 18 in lens 12 to the other. Wire 20 may, as already mentioned, be formed of metal or plastic.

The diametral size $d_1$ of wire 20 is preselected to be greater than the diametral dimension $d$ of holes 18 to the extent that when subsequently forced through holes 18 it will produce an interference fit in lens 12 which can be depended upon to remain secure, i.e., not become detached, throughout the expected useful life of pseudophakos 10. Exemplary diametral sizes of holes 18 and wire 20 are respectively 0.10 mm and 0.13 mm. Other hole and wire sizes and/or size differentials may, of course, be used to meet particular requirements and the present invention is not intended to be restricted by any dimensions set forth herein. All such dimensions are given for purposes of illustration only.

Figure 5:
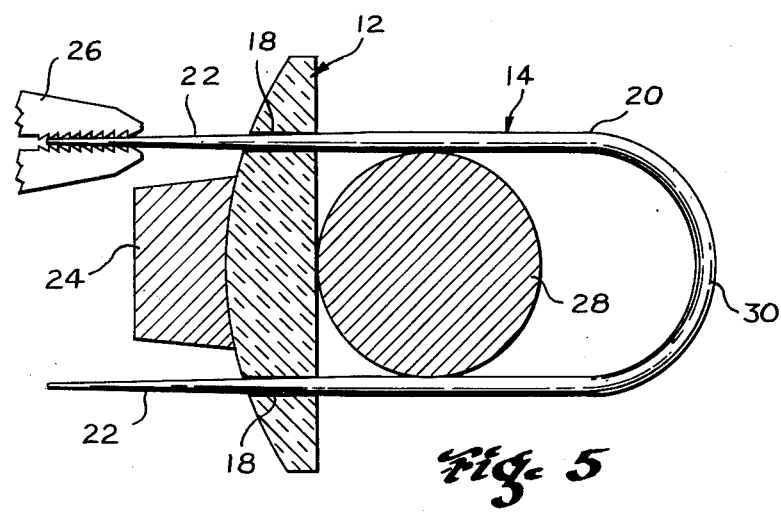

Portions of the length of wire 20 adjacent its opposite ends are reduced to diametral dimension $d_2$ to form leaders 22. This may be accomplished by immersing the portion of the wire to be reduced into a suitable etching medium, e.g., dilute hydrochloric or other acids, for a period of time controlled to etch the same to the desired reduced diametral size or by peening, rolling or drawing the portion to be reduced. In one or more of the latter cases, the wire may be heated to facilitate its size reduction. An exemplary diametral size $d_2$ for leaders 22 may be 0.08 mm or a reduction of approximately 0.05 mm from the initial exemplary wire size of 0.13 mm. In any case, the diametral size of leaders 22 is, according to the invention, such that they can be readily "threaded" through holes 18 and thereby lead their adjoining larger diameter portion of wire 20 into holes 18 for force fitting. Leaders 22 may be uniformly tapered from diameters $d_1$ to $d_2$ as shown in FIG. 4 or tapered only in a transition zone adjacent the larger diameter $d_1$. Force fitting of wires 20 is accomplished as follows:

Referring more particularly to FIG. 5, a clip 14 is applied to lens 12 by directing tapered leaders 22 of wire 20 through holes 18 to a point on the leaders where interference occurs within holes 18. Thereafter, with lens 12 supported by a rest or anvil 24, leaders 22 are gripped (e.g., with pliers 26) and the larger diameter portion of wire 20 is pulled, preferably completely through holes 18 to the extent illustrated in FIG. 6, for example. It should be understood, however, that this operation may be performed by holding the gripped ends of leaders 22 stationary and forcing lens 12 with anvil 24 over the larger diameter portion of wire 20. In either case, a loop-forming mandrel 28 may also be used if desired to produce the final configuration of bight 30 of the resulting iris clip 14.

Having thus fastened wire 20 of iris clip 14 to lens 12 with the interference fit in holes 18, leaders 22 are cut away at convenient points and discarded. Broken line 32 in FIG. 7 and the already cut-away leader 22' depict desirable cutting locations.

In order to prevent interference of the remaining cut ends of wire 20 with portions of the interior of a recipient eye 16, for example, these ends may be recessed into holes 18 of lens 12 either by forcefully drawing lens 12 back upon clip 14 or driving ends 34 partially into holes 18 with a suitable punch 36 of other setting tool.

A second similar iris clip 14 may be similarly applied to lens 12 for finishing pseudophakos 10.

Having so permanently affixed clips 14 to lens 12 with the forced interference fit of wires 20 in holes 18, it remains only to shape the clips by bending to a desired lateral and slightly rearwardly tending direction as illustrated with broken lines 14' in FIG. 9.

Without attempting to illustrate all of the various other forms of pseudophakoi to which the technique of this invention is applicable, FIGS. 10–12 may be considered as exemplifications thereof.

In FIG. 10, there is illustrated the "iris clip" type of pseudophakos having a pair of anterior iris clips 38 and a pair of posterior iris clips 40, all of which may be fastened to lens 10' in the manner described hereinabove relative to clips 14 of pseudophakos 10.

A pseudophakos 10″, generally similar to pseudophakos 10, is illustrated in FIG. 11. Pseudophakos 10″ is provided with one pair of posterior iris clips 42 for insertion into the iridocapsular cleft and additionally has a wire clasp 44. Iris clips 42 and clasp 44 may each be affixed to the lens portion of pseudophakos 10″ in the manner of the present invention. In use, clasp 44 of pseudophakos 10″ is normally extended anteriorly of the iris of a recipient eye, passed through an iridectomy and fastened to its adjacent posterior iris clip 42. This guards against undue luxation of the pseudophakos in use.

A still further exemplary type of pseudophakos to which the practice of the present invention is applicable comprises lens 46 (FIG. 12) having posterior iris clips 48 which are in the usual configuration of loops and anterior iris clips 50 each formed into the configuration of a strut. Anchoring of these posterior and anterior iris clips to lens 46 may be accomplished in the manner of the present invention for providing both the surgeon and the patient with an assurance against accidental loosening or disconnection from the lens.

FIGS. 13, 14 and 15 are illustrations of an application of the present method to installation of anterior iris clips in an edge of a lens. A pseudophakos 52 of such construction is depicted in FIGS. 13–15.

Pseudophakos 52 having the usual posterior iris clips 54 (FIGS. 13 and 14) installed as described above, is further provided with a pair of intersecting chordal openings 56a, 58a and 56b, 58b at each of diametrically opposite sides thereof (FIG. 15).

Wires 60 and 62 (FIG. 15) used to form oppositely disposed anterior iris clips 64 and 66 respectively of pseudophakos 52 are initially provided with tapered leaders 68 at each of their opposite ends. Leaders 68 are each of a size and length readily insertable into and through one of openings 56a, 58a, 56b, or 58b whereafter they may be gripped for pulling the full or maximum diameter portion of wires 60 and 62 into a respective opening to produce a desired interference fit of the wire therewithin. This tapered portion 68 is then cut away, e.g. at line 70, FIG. 15, and discarded whereafter the wire is retracted into the hole to recess its cut end.

After so fixing each of opposite ends of clips 62 within the lens of pseudophakos 52, the clips may then be finally shaped by bending adjacent their respective points of entrance into the lens.

The particular illustrations of practice of the invention and exemplary forms of pseudophakoi here shown are not to be interpreted as restrictive of the invention beyond that necessitated by the following claims. Those skilled in the art will readily appreciate that there are various modifications and adaptations of the aforesaid precise forms of the invention here shown which may be made to suit particular requirements.

I claim:

1. The method of securing iris clips to lenses of pseudophakoi wherein the iris clips are formed of wire and anchoring holes are provided in the lenses for receiving ends of the wires, said method comprising the steps of:
    providing a wire having a substantially uniform preselected diametral size at least throughout a selected portion of its length to be secured to a lens, said selected portion having a first free end;
    forming a hole in said lens of an appreciably smaller diametral size than the diametral size of said selected portion of said wire, the differential of diametral sizes of said hole and portion of said wire being sufficient to prevent accidental detachment of lens and wire following forceful interfitting thereof;
    reducing the diametral size of a section of said selected portion of said wire adjacent said first free end to at least the diametral size of said hole to produce an integral leader on said selected portion of said wire, said leader being easily manually insertable through said hole in said lens and further being of a length adapted to extend entirely through said hole from a first side of said lens to an opposite second side and beyond;
    directing said leader into and completely through said hole in said lens from said first side through said second side;
    gripping said leader and forcing said portion of said wire of said preselected diametral size and said lens relative to one another into interference interfitted relationship, a substantial portion of said leader adjacent said second side of said lens becoming exposed; and
    cutting away and discarding an exposed portion of said leader then forcefully retracting the remaining exposed portion of said leader into said hole.

2. The method according to claim 1 wherein at least a second hole is formed in said lens and said wire is provided with a second selected portion having a second free end and second leader adjacent said second free end, said second hole, second portion and second leader are substantially dimensionally identical to cognate first element and interfitted by the practice of the same method steps as for the first free end wherein said wire, so fitted to said lens, is in the configuration of a loop having a bight intermediately of its attachments to said lens.

3. The method according to claim 2 wherein said loop is forced against a shape-forming mandrel at one stage of the wire and lens interfitting process to impart a desired shape to said bight.

4. The method according to claim 2 wherein said holes number four and an additional wire is provided to produce a pseudophakos having a pair of iris clips according to the aforesaid method.

5. The method according to claim 4 wherein still additional holes and wires are applied to said lens according to the aforesaid method.

6. The method according to claim 1 wherein said step of forcing said portion of said wire and said lens into interference interfitted relationship is accomplished by pulling said wire through said hole.

7. The method according to claim 1 wherein said step of forcing of said portion of said wire and said lens into interference interfitted relationship is accomplished by moving said lens over said wire.

8. The method according to claim 2 wherein said wire is of said preselected diametral size throughout its entire extension between said leaders.

* * * * *